United States Patent
Alaux et al.

(10) Patent No.: US 6,514,531 B1
(45) Date of Patent: Feb. 4, 2003

(54) CONTROLLED-RELEASE DOSAGE FORMS COMPRISING ZOLPIDEM OR A SALT THEREOF

(75) Inventors: Gérard Alaux, Beynes (FR); Gareth Lewis, Dourdan (FR); Frédéric Andre, Antony (FR)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 09/857,154

(22) PCT Filed: Dec. 1, 1999

(86) PCT No.: PCT/EP99/10454
§ 371 (c)(1),
(2), (4) Date: Jul. 16, 2001

(87) PCT Pub. No.: WO00/33835
PCT Pub. Date: Jun. 15, 2000

(30) Foreign Application Priority Data

Dec. 4, 1998 (EP) ............................... 98403037

(51) Int. Cl.[7] .............. A61K 9/22; A61K 9/48; A61K 9/26; A61K 9/52; A61K 9/16
(52) U.S. Cl. ............ 424/468; 424/451; 424/457; 424/464; 424/469; 424/470; 424/471; 424/472; 424/474; 424/489; 424/490
(58) Field of Search .................. 424/451, 457, 424/464, 468, 469, 470, 471, 472, 474, 489, 490

(56) References Cited

U.S. PATENT DOCUMENTS 5,629,017 A * 5/1997 Pozzi et al. .................. 424/476
6,309,668 B1 * 10/2001 Bastin et al. ................ 424/472
6,372,255 B1 * 4/2002 Saslawski et al. .......... 424/473

FOREIGN PATENT DOCUMENTS

| EP | 173 928 | 8/1985 |
| EP | 0 173 928 | * 12/1986 |
| EP | 361 910 | 9/1989 |
| EP | 0 361 910 | * 4/1990 |
| GB | 2 245 492 | 7/1991 |
| WO | 95/20947 | 1/1995 |

* cited by examiner

Primary Examiner—Thurman K. Page
Assistant Examiner—S. Tran
(74) Attorney, Agent, or Firm—Paul E. Dupont; Michael D. Alexander

(57) ABSTRACT

The present invention relates to controlled-release dosage forms of zolpidem or salts thereof adapted to release zolpidem over a predetermined time period, according to a biphasic profile of dissolution, where the first phase is an immediate release phase and the second phase is a prolonged release phase and particular embodiments thereof intended to avoid abuse.

47 Claims, 11 Drawing Sheets

CONTROLLED-RELEASE DOSAGE FORMS COMPRISING ZOLPIDEM OR A SALT THEREOF

This application is a 371 of PCT/EP99/10454 filed Dec. 1, 1999.

The present invention relates to controlled-release dosage forms comprising zolpidem or salts thereof.

BACKGROUND OF THE INVENTION

EP 173 928 discloses an oral pharmaceutical controlled release preparation which has a biphasic release profile of a pharmacologically active agent, comprising a core containing the active agent and a coating applied thereon, wherein the coating consists of a film-forming polymer which is insoluble in water and gastro-intestinal fluids and a water-soluble pore-creating material also including the active agent.

EP 361 910 discloses granules which have a spray-dried substance carrying an adsorbed pharmaceutical and a layer comprising a pharmaceutically acceptable excipient and a pharmaceutical.

GB 2 245 492 discloses an orally administrable programmed release (i.e. release after a predetermined delay) pharmaceutical preparation comprising a core coated with a hydrophobic material and a surfactant.

BRIEF DESCRIPTION OF THE INVENTION

Zolpidem is a suitable short acting hypnotic for the controlled-release dosage form according to the present invention. Zolpidem is a hypnotic from the therapeutical class of imidazopyridines. It is administrated orally by means of a tablet or other solid dosage form. Zolpidem acts rapidly. Indeed pharmacokinetic and pharmacodynamic data show that zolpidem has both a rapid absorption and onset of hypnotic action. Its bioavailability is 70% following oral administration and demonstrates linear kinetics in the therapeutical dose range, which lies between 5 and 10 mg in conventional forms, peak plasma concentration is reached at between 0.5 and 3 hours, the elimination half-life is short, with a mean of 2.4 hours and a duration of action of up to 6 hours.

For reasons of simplicity, in the absence of contrary indication, within the whole description "zolpidem" or the "drug" means zolpidem per se as well as its salts. The preferred salt of zolpidem is zolpidem hemitartrate.

Up to now, according to the rapidity of action of zolpidem, only immediate release dosage forms were developed, which disintegrate rapidly in the gastrointestinal tract, dissolve in the fluid of the gastrointestinal tract and undergo systemic absorption, where zolpidem, can exert its pharmacological effect and induce sleep of the patient.

The new dosage forms according to the present invention enable to sustain release over a period compatible with the desired time of sleep and the time needed for elimination of the drug from the human body to a sufficiently low level.

Therefore, as a first object, the present invention provides controlled-release dosage forms comprising zolpidem or salts thereof adapted to release over a predetermined time period, according to a biphasic profile of dissolution, where the first phase is an immediate release phase and the second phase is a prolonged release phase.

The "total amount of drug" means the quantity by weight of the drug comprised in the whole dosage form according to the invention.

The first phase or immediate release phase is that part of the dissolution profile from 0 to 30 minutes in a suitable in vitro dissolution test. A suitable dissolution test is for example one of the method described in example 1: method where measurement is carried out in a type II dissolution apparatus according to U.S. pharmacopoeia in aqueous buffer at 37° C., or variations on this as well known to one who is skilled in the art. The proportion of the drug dissolved during this phase is the proportion of the total amount of the drug which is dissolved at 30 minutes. In an advantageous embodiment of the dosage forms according to the present invention 90% or more of that part of the drug allotted for the first phase is dissolved in 20 minutes and more preferably in 15 minutes.

The second phase or prolonged release phase is that part of the dissolution profile which is after 30 minutes, measured in a suitable in vitro dissolution test, such as described in example 1. The present invention then proposes dosage forms of the drug whose complete dissolution time for the second phase is between 2 and 6 hours, and preferably between 2.25 and 3.5 hours.

The profile of the second, prolonged release phase is defined by the percentage released at times $T_1$, $T_2$, and $T_3$, defined as follows.

$T_1$ is the beginning of the second phase of drug release, and is equal to 30 minutes.

$T_3$ is near the end of the second phase of drug release, and is the time at which 85% of the drug allotted for the second phase is released.

$T_2$ is the time at which 50% of the drug allotted for the second phase is released. For example, if 50% of the total amount of drug is released at 30 minutes, there is 50% remaining for the second phase of release. $T_3$ is therefore the time for 92.5% dissolution [50%+0.85× 50%], and $T_2$ is the time for 75% dissolution.

The second phase can represent a profile of release proportional to the square root of time, according to the equation proposed by T. Higuchi, *J.Pharm.Sci.* 52, 1145 (1963), sometimes called matrix release, where $(T_2-T_1)=0.35(T_3-T_1)$. More advantageously the second phase can be first-order release where $(T_2-T_1)=0.37(T_3-T_1)$. Still more advantageously the second phase can represent a profile of order zero or a sigmoidal profile. A profile of order zero is one where the release rate is constant or near-constant, and $(T_2-T_1)=0.59(T3-T_1)$. A sigmoidal profile is one where the release rate in the second phase accelerates so $(T_2-T_1)>0.59(T_3-T_1)$. Profiles intermediate between these different types are also covered.

The rapid release in the first phase induces the immediate sleep of the patient and the second phase allows the drug blood level to be maintained at or below the peak level, but higher than the level obtained with an immediate release dosage form, at the same time after dosing, with the objective of maintaining sleep.

The present invention then proposes dosage forms of zolpidem or a salt thereof whose complete dissolution time, defined as the time for release of 90% of the total amount of drug is between 2 and 6 hours and preferably between 2.25 and 3.5 hours.

40 to 70% of the total amount of drug can be released during the immediate release phase, preferably between 50 and 60%.

An example of such an in vitro release profile is given in FIG. 1, where 60% of the total amount of drug is released during the immediate release phase, and the second phase is zero order with 90% of the total amount of drug dissolved in 3 hours. Further examples of such profiles are shown in FIG. 2, where 50% of the total amount of drug is dissolved during the immediate release phase, and the second phase release is according to three other types of profile; release proportional to square root of time (matrix release), first order release, and a sigmoidal release profile.

As a second object, the present invention provides controlled-release dosage forms of zolpidem or salts thereof, characterised in that they comprise two kinds of pharmaceutical entities of drug: one immediate release entity and one prolonged release entity. The drug dissolved during the immediate release phase (before 30 minutes) is contained within the immediate release entity, and that liberated in the prolonged release phase (after 30 minutes) is contained within the prolonged release entity.

Small quantities of the drug in a formulation for rapid release can be retained in the formulation and thus may be released at a time after 30 minutes from the beginning of the dissolution, and are thus included in the prolonged release phase. Similarly, small quantities of the drug incorporated in the prolonged release pharmaceutical entity may be released before 30 minutes, and thus form part of the immediate release phase.

According to the present invention, the proportion of the drug contained within the immediate release entity and dissolved within 30 minutes is at least 90%. And the proportion of the drug contained within the prolonged release entity and released within 30 minutes is comprised between 0 and 35%, and preferably between 0 and 25%.

Among dosage forms able to match the requirement of a biphasic profile and to comprise the two kinds of pharmaceutical entities defined above, the following may be cited: capsules, tablets, multilayer tablets, multicoated tablets.

The immediate release entity shall be understood in the present invention as a single pharmaceutical immediate release unit like for example an immediate release tablet or pellet, or several such units formulated into a capsule or a tablet; as an immediate release matrix in a tablet; as an immediate release layer, that can be incorporated in a multilayer tablet; as an immediate release coating layer in a multicoated tablet or pellet.

The prolonged release entity shall be understood in the present invention as a pharmaceutical prolonged release unit such as, for example, a prolonged release tablet or pellet, or several such units formulated into a capsule or a tablet; as a prolonged release layer, that can be incorporated in a multilayer tablet; as a prolonged release core or a prolonged release coating layer in a multicoated tablet; as prolonged release pellets within a disintegrating tablet.

Dosage forms where the immediate release entity and the prolonged release entity are administered simultaneously but separately are also encompassed in the present invention.

DETAILED DESCRIPTION OF THE INVENTION

Figure 1:
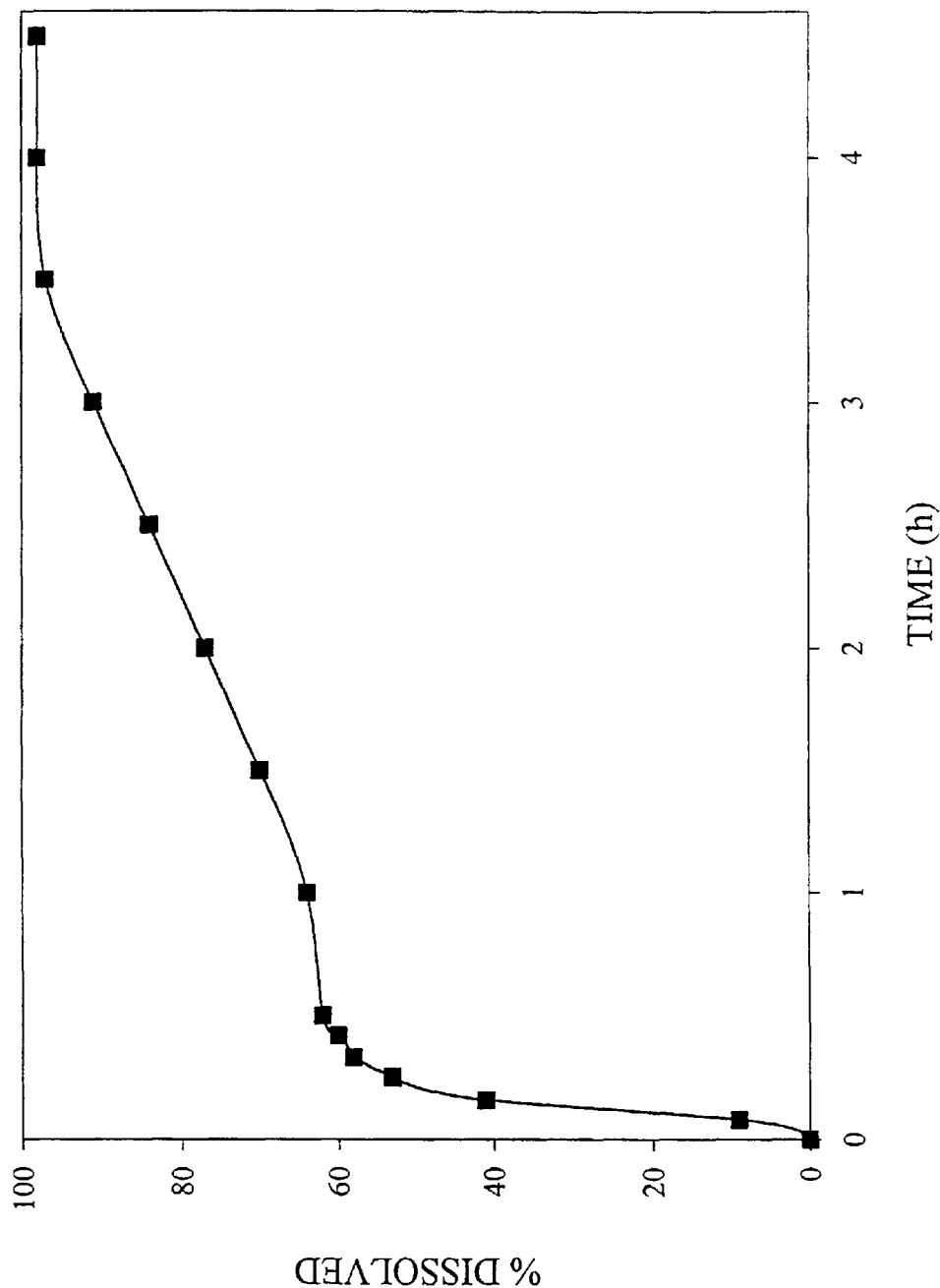
FIG. 1 shows an example of a in vitro biphasic release profile, where the immediate release phase is 60% of the total amount of zolpidem, and the second phase is zero order with 90% of the total amount of zolpidem dissolved in 3 hours.
Figure 2:
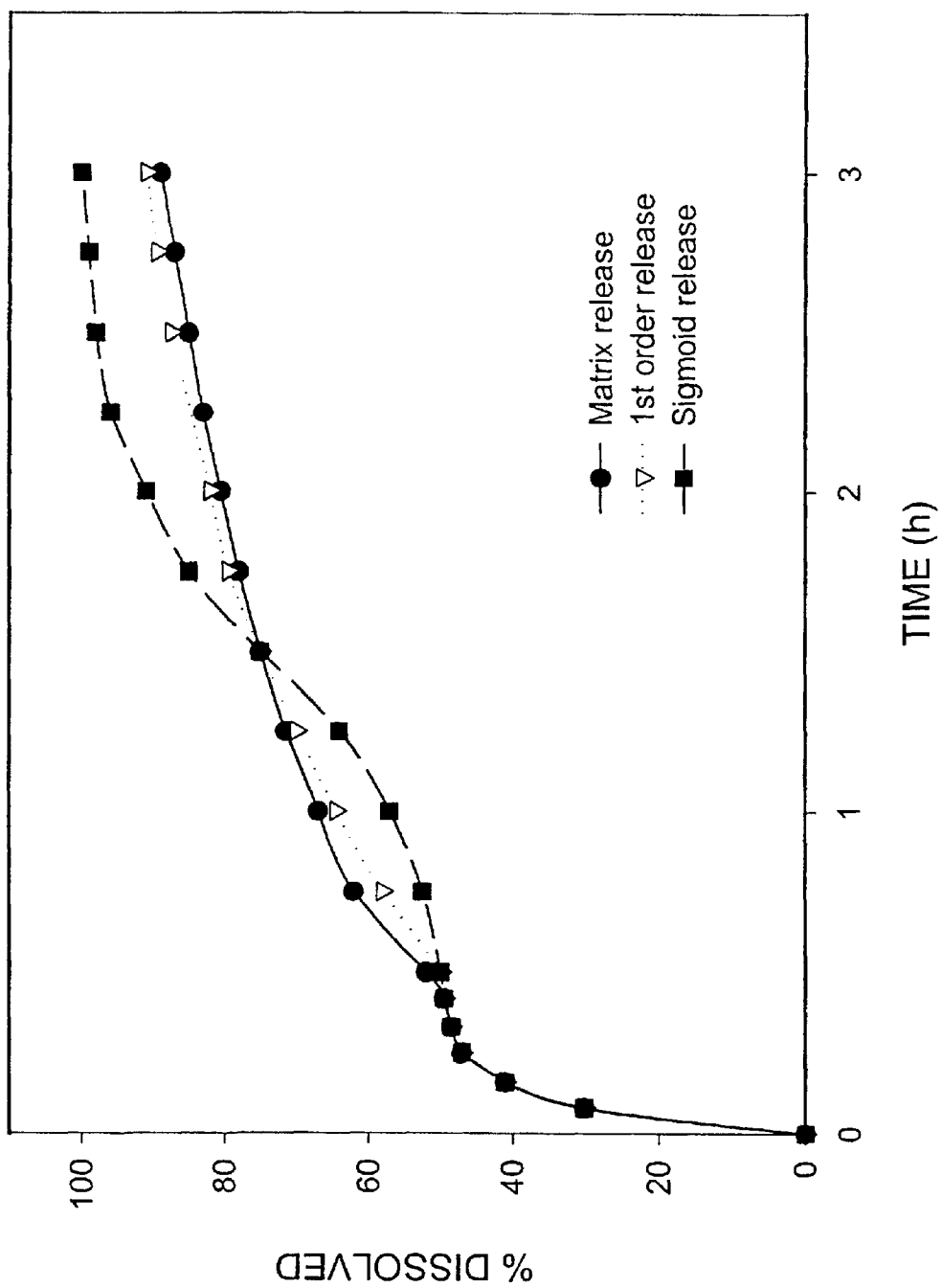
FIG. 2 shows an examples of biphasic in vitro release profiles, where 50% is dissolved in the first phase, and the second phase release is (i) proportional to the square route of time (continuous line), (ii) first order (dotted line), and (iii) a sigmoid release profile (dashed line)

The dosage forms according to the invention typically contain from 4 to 16 mg of zolpidem as zolpidem base, and preferably 6 to 12 mg of zolpidem as zolpidem base. The zolpidem may be incorporated as the base, or as a pharmaceutically acceptable salt of zolpidem. Among dosage forms comprising a salt of zolpidem rather than the zolpidem base, according to the invention, those comprising zolpidem hemitartrate are especially preferred.

In advantageous embodiments, dosage forms may be formulated in order to obtain in the second phase a dissolution independent of the pH. The preferred manner to achieve such a dissolution, in the case of basic drugs like zolpidem is to add a pharmaceutically acceptable organic acid into the dosage form, according to methods known from one skilled in the art. Such dosage forms are preferred.

These pharmaceutically acceptable organic acid can be chosen for example among maleic, tartaric, malic, fumaric, lactic, citric, adipic or succinic acid and their acid salts where these exist, in the form of racemates or isomers, where these exist. According to the invention, acids particularly preferred are tartaric, fumaric, citric, and succinic and their acid salts.

Various formulations, not limiting the scope of the present invention, illustrating the invention are described hereafter:

(1) A capsule comprising one or more immediate release tablets and one or more prolonged release tablets:

Immediate release tablets may be prepared by direct compression of mixtures of the drug or salts thereof with diluents, such as microcrystalline cellulose, mannitol, sorbitol, and lactose. Other functional excipients such as disintegrants and lubricants can be added. Choice of these functional excipients as well as diluent is well known to anyone skilled in the art. Alternatively tablets may be prepared by granulation with water of a mixture of the drug or salts thereof with suitable diluents, disintegrant and binding polymer; calibration and drying of the granulate addition of a lubricant, followed by compression on a tableting machine. The methods used are those generally described in the pharmaceutical literature, see for example, B. B. Sheth, F. J. Bandelin and R. JF. Shangraw, Compressed Tablets, in Pharmaceutical Dosage Forms: Tablets, Vol 1. edited by H. A. Lieberman and L. Lachman, Dekker N.Y. (1980).

Prolonged release tablets can be prepared by coating immediate release tablets with a diffusion limiting polymer coating. Suitable polymers can be chosen among ethyl cellulose, methyl methacrylate copolymers, such as Eudragit® RS, Eudragit® RL, Eudragit® NE commercialized by Röhm Pharma. Coating methods can consist in spraying a solution of the polymer on the tablets, either in a pan coater or a fluid bed coating apparatus. The solvent may be organic or aqueous, depending on the nature of the polymer used. Coating methods are described in the following works: J. M. Bakan, Microencapsulation, in L. Lachman, H. Lieberlmman and J. L. Kanig (Eds.) The Theory and Practice of Industrial Pharmacy, Lea & Febinger, Philadephia, USA, 1986 ; J. M. McGinity, Aqueous polymer coatings for Pharmaceutical Dosage Forms, Dekker N.Y., 1989. Alternatively prolonged release tablets can be prepared by incorporating matrix-forming excipients into the formulation, and omitting disintegrants. Such matrix-forming excipients may be hydrophilic polymers, which include hydroxypropylmethylcellulose, hydroxymethylcellulose, hydroxyethylcellulose, and which swell in contact with aqueous liquids, and control release of the drug by diffusion through the swollen polymer network, and are incorporated at a level between 10 and 30% by weight with respect to that of the prolonged release tablet.

Otherwise the matrix forming excipient may be a lipidic substance, such as hydrogenated castor oil, or carnuba wax, incorporated at a level between 10 and 40% by weight with respect to that of the prolonged release tablet.

Prolonged release tablets can be formulated, as zolpidem is a basic drug optionnally with a pharmaceutically acceptable organic acid, chosen from the list given above so as to maintain the micro-pH of the tablet during dissolution in the neutral pH conditions of the small intestine.

(2) A capsule comprising a mixture of prolonged release pellets and immediate release pellets:

The immediate release pellets may be prepared by deposition of the drug suspended in water or an organic solvent such as ethanol with hydroxypropylmethylcellulose or povidone or another suitable polymer to act as a binder, onto a spherical granule. A fluid bed coating apparatus is generally used. Particles may be agglomerated to form spherical granules or pellets, in a high speed mixer granulator, or rotary fluid bed agglomerator. These methods are described by K. W. Olson and A. M. Mehta, Int.J.Pharm.Tech&.Prod.Mfr. 6 18–24, 1985. Pellets may be also prepared by extrusion of wet masses or melts followed by spheronisation, for example as described in C. Vervaet, L. Baert & J. P. Remon *Int.J.Pharm.* 116 (1995) 131–146. Excipients used are typically those with plastic qualities such as microcrystalline cellulose, but also mannitol. Small quantities of a polymeric binder are generally added. Surfactants such as sodium dodecyl sulphate may also be incorporated to give easier extrusion.

Prolonged release pellets are prepared by coating immediate release pellets in the same way as described for the tablets. Coating may be carried out, for example, in coating pans or in fluid bed coater-driers. The amount and composition of the coating is adjusted from that used in the tablet, to reduce the permeability of the coating in order to take into account the far greater surface for diffusion in the pellets.

Prolonged release pellets can, as zolpidem is a basic drug, contain a pharmaceutically acceptable organic acid so as to maintain the micro-pH of the interior of the pellet during dissolution in the neutral pH conditions of the small intestine.

Alternatively, as zolpidem is a basic drug, prolonged release pellets may be coated with a pH sensitive membrane, containing polymers soluble at neutral pH and impermeable at acid pH, such as Eudragit® S, allowing increased permeation by the drug at pH 5 and above, to compensate for the decreased solubility of the drug at higher pH values. Alternatively sustained release pellets and immediate release powder.

(3) A tablet comprising a number of prolonged release coated pellets comprising the drug imbedded in a matrix also comprising the drug:

Alternatively the tablet may consist of a mixture of prolonged release coated pellets and of immediate release non-coated pellets comprising the drug, imbedded in a drug-free matrix.

Alternatively the prolonged release coated pellets may be furthermore coated with a layer comprising the drug and other excipients allowing immediate release from that layer, imbedded in a drug-free matrix.

The matrix surrounding the pellets should preferably be formulated so that the compression into tablets does not interfere with the integrity of the membrane surrounding the pellets. On contact with fluid the tablet disintegrates, releasing the drug rapidly, from the matrix, or the immediate release pellets, or from the immediate release pellet coating, and then releasing the drug from the prolonged release pellets slowly. The pellet may be formulated with a pharmaceutically acceptable organic acid so as to maintain the micro-pH of the pellet during dissolution in the neutral pH conditions of the small intestine.

(4) A multilayer tablet comprising:

(i) one or two prolonged release layers, comprising the drug and a hydrophilic polymer (preferably a cellulose derivative), (ii) one or more immediate release layers comprising the drug, and possibly, (iii) another layer not comprising the drug, but comprising hydrophilic polymers, such as hydroxypropylcellulose, hydroxypropylcellulose, hydroxyethylcellulose or soluble diluents, such as lactose, sorbitol, mannitol, or hydrophilic polymers and soluble excipients, which layer modulates release of the drug from the prolonged release layer.

Each layer contains other excipients, so as to give suitable properties for compression, lubrification, binding as is well known to one skilled in the art. Examples of such bilayer and multilayer tablets are shown in FIG. 7*a–d*, where immediate release layers are designated by i, prolonged release layers by p and layers modulating the release profile by m.

(5) A multicoated tablet comprising:
(i) a core comprising the drug and as zolpidem is a basic drugs, optionnally a pharmaceutically acceptable organic acid to maintain constant pH,
(ii) a polymer coating layer giving slow release of the drug from this core,
(iii) a coating layer comprising the drug which is released rapidly or immediately on contact of the dosage form with fluid.

Each portion of the tablet, in particular the inner core, can contain other excipients, so as to give suitable properties for compression, lubrification, and binding as is well known to one skilled in the art. Methods for making both multilayered and multicoated tablets are described by W. C. Gunsel, Compression coated and layer tablets in Pharmaceutical Dosage Forms: Tablets, Vol 1. edited by H. A. Lieberman and L. Lachman, Dekker N.Y. (1980).

As other particular embodiments encompassed within the scope of the present invention, pharmaceutical compositions intended to avoid abuse may be cited.

Indeed it is known that some drugs and in particular hypnotics intended for legitimate oral use have the potential for abuse.

One way of substantially reducing or even eliminating this potential for drug abuse for the pharmaceutical formulations that are objects of the present invention is to provide pharmaceutical compositions for oral administration comprising zolpidem capable at the same time of:

liberating the active principle according to a biphasic in vitro profile as described above, following normal administration and, if it is introduced in a drink, whether or not containing alcohol, generating visual change or changes in the appearance of the drink. This visual change or changes are intended to avoid administration of the active principle to a person in the said drink without his or her knowledge.

These visual changes, according to the present invention include all means of indicating the presence of the said composition in a drink. The following may be cited as methods for inducing visual changes: inclusion of colouring excipients, floating of the composition at the surface of the drink, formation of insoluble particles on the surface of the drink, on the brim of the glass, in the drink and/or on the bottom of the glass or a combination thereof. The drink, eventually with alcohol, may for example consist of coffee, tea, wine, fortified wine, spirits, liqueurs, hot or cold chocolate-flavoured drinks, all gaseous alcoholic or not-alcoholic drinks, all cocktails or mixtures of fruit juice, milk, cream, . . .

Floating of the composition can be achieved by an effervescence which can be obtained by means of a effervescence generator, as described hereinafter. In addition to these effervescent properties, the composition can present viscosity increasing properties appearing on contact with the drink. Thus when the bubbles are formed, they are "trapped" and the composition swells. The lowering of the density contributes to maintaining the pharmaceutical composition at the surface of the drink. Such a viscosity may be obtained by one or more gelating substances. Hydrophilic excipients are particularly suitable as gel-forming substances as set forth beneath.

Particles may be obtained by association of a lipophilic and a hydrophilic excipient, useful for the floating as described above. A list of suitable lipophilic excipients is set forth beneath.

The composition according to this particular embodiment of the present invention can liberate particles even if the composition does not float or not immediately.

The effervescence generator can be a carbon dioxide generator system. It can comprise a suitable carbon dioxide generator agent and a pharmceutically acceptable acid.

The carbon dioxide generator agent is normally a carbonate or bicarbonate of an alkali or alkaline earth metal or an amino acid. Calcium carbonate, sodium bicarbonate, potassium carbonate, potassium bicarbonate, L-lysine carbonate, arginine carbonate or sodium sesquicarbonate may be cited as carbon dioxide generator agents.

The acid may be an acid anhydride, a monocarboxylic acid, a polycarboxylic acid or a partial salt of a polycarboxylic acid. More particularly citric, tartric, ascorbic, fumaric, nicotinic, acetysalicylic, maleic, adipic, succinic, malic, malonic acid may be chosen or glutaric anhydride, citric anhydride, monosodium citrate and succinic anhydride.

The carbon dioxide generator agent may be constituted by a mixture of carbon dioxide generating agents cited above.

In such a carbon dioxide generator system, the content of acidic compound is generally chosen such as the ratio between the number of moles in the said acidic compound with respect to the number of moles in the said carbon dioxide generator agent is between 1 and 2.

The gel forming substances can consist of one or more hydrophilic excipients provoking the swelling of the composition and the trapping of the gas released. In order to form insoluble particles, one or more lipophilic excipients are added to the hydrophilic excipient.

The process of effervescence and formation of particles generate viscous agglomerates which float and stick to the glass. This process can last between 0.5 and 25 minutes depending on the type of drink.

Among lipophilic excipients the following may be cited: glycerol stearates, palmitostearates and behenates; hydrogenated vegetable oils and their derivatives; vegetable and animal wax and their derivatives; hydrogenated castor oils and their derivatives and cetylic esters and alcohols.

Among hydrophilic excipients the following may be cited: cellulose derivatives, hydroxyethylcellulose, hydroxypropylcellulose (molecular mass from 50 to 1250 kDa), hydroxypropylmethylcellulose (molecular mass from 10 to 1500 kDa), carboxymethylcellulose and sodium carboxymethylcellulose; vegetable gums and their derivatives; derivatives of alginic acid; polyethyleneglycols and their derivatives; starches and their derivatives; silica, polymethacrylates and acrylic acid and methacrylate copoplymers.

One of the constituants of the gel forming substance can be chosen as being less soluble in alcohol.

A colouring excipient can be advantageously added as giving rise to visual change preventing abuse. It can colour simultaneously the liquid or the particles or one independantly of the other.

Among suitable colouring excipients the following may be cited: indigotine, cochineal carminic acid, yellow orange S, allura red AC, iron oxides, cucurmin, riboflavin, tartrazine, quinoline yellow, azorubine, amaranth, carmines, erythosine, red 2G, patented blue V, glittering blue FCF, chlorophylls, copper complexes of chlorophylls, green S, caramel, glittering black BN, carbo medicinalis vegetabilis, brown FK and HT, carotenoids, Annatto extracts, paprika extracts, lycopene, lutein, canthaxanthin, beetroot red, anthocyanes, calcium carbonate, titanium dioxide, aluminium, silver, gold or litholrubin BK or any other colouring excipient suitable for an oral administration.

These visual means of preventing abuse may comprise a distinct pharmaceutical entity, not containing active substance, along with the immediate release and the sustained release entities, that comprise the pharmaceutical form, or they may be incorporated in one of these two entities. Yet a third method is to incorporate all or certain of them into a separate entity and at the same time add certain to the immediate or sustained release entity.

The method of incorporation of abuse resistance as described above will depend on the type of formulation. In the case of tablet formulations described above, including that of tablets enclosed inside a capsule, the abuse resistance confering substances (colouring matter, effervescent couple . . . ) may be included within the immediate release entity of the formulation.

Alternatively in the case of multilayer tablets and immediate tablets within a capsule they may be incorporated as a separate layer not containing active substance, but with the abuse resistance confering substances. Such a layer may be added to the sustained release tablet or tablets within a capsule provided the said tablet is formulated as a matrix and is not coated with a coating confering the sustained release properties.

In the case of a capsule containing controlled release pellets and immediate release pellets or granulate, abuse resistance confering substances with the exception of an effervescent couple may be incorporated in the immediate release entity or added separately.

The examples which follow illustrate the invention without limiting it:

EXAMPLE 1

Prolonged release tablet comprising 10 mg zolpidem hemitartrate.

The first four of the following materials were mixed together, granulated with water, dried and calibrated. The granulate was then mixed with the magnesium stearate and compressed to a mass of 120 mg per tablet, using a rotary tableting machine.

| | |
|---|---|
| zolpidem hemitartrate | 8.3% |
| lactose | 86.6% |
| citric acid | 2.5% |
| hydroxypropylmethylcellulose 606[1] | 2.1% |
| magnesium stearate | 0.5% |

[1]Pharmacoat 606, commercialized by Shin-Ensu Co

Tablets were coated, in an Accelacota pan coater, with a sufficient quantity of the following mixture to obtain the desired dissolution profile.

| | |
|---|---|
| ethylcellulose[1] | 2.0% |
| diethylphthalate | 0.4% |
| hydroxypropylmethylcellulose 606 | 2.0% |
| isopropanol | 47.8% |
| dichloromethane | 47.8% |

[1]Ethocel, commercialized by Dow Chemical Co.

Figure 3:
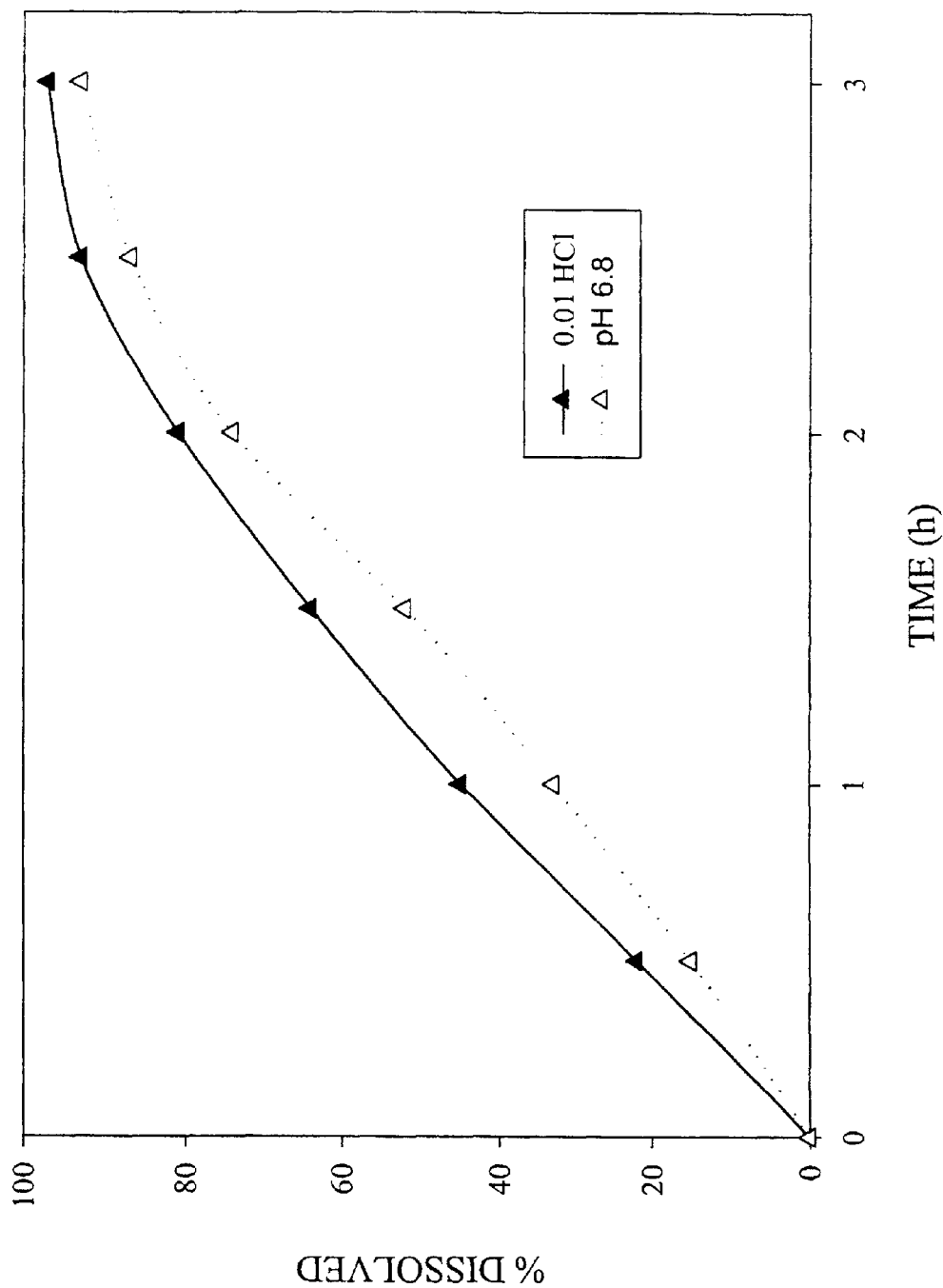
FIG. 3 shows an in vitro dissolution profile of the tablets of example 1, in 0.01 M hydrochloric acid and in pH 6.8 phosphate buffer, as described in example 1.

The in vitro dissolution profiles of the tablets were established using the Apparatus II of the United States Pharmacopoeia. Two dissolution media were employed: 900 ml hydrochloric acid 0.01 M and 900 ml of a pH 6.8 potassium phosphate 0.05 M buffer, maintained at 37±0.5° C. Stirring was by the paddle method (50 rpm). The percentage dissolved was determined by measurement of the UV absorbance at 270 nm (continuous sampling by a peristaltic pump in a closed system). The results are shown in FIG. 3.

Comparative Example 1

Prolonged release tablet without acid comprising 10 mg zolpidem hemitartrate.

Tablets were manufactured according to the same method as example 1, having the following composition:

| | |
|---|---|
| zolpidem hemitartrate | 8.3% |
| lactose | 89.1% |
| hydroxypropylmethylcellulose 606 | 2.1% |
| magnesium stearate | 0.5% |

They were coated with a polymer mixture comprising 50% hydroxypropylmethylcellulose and 50% ethylcellulose. Their in vitro dissolution profiles of the tablets were established by the method of example 1.

Figure 4:
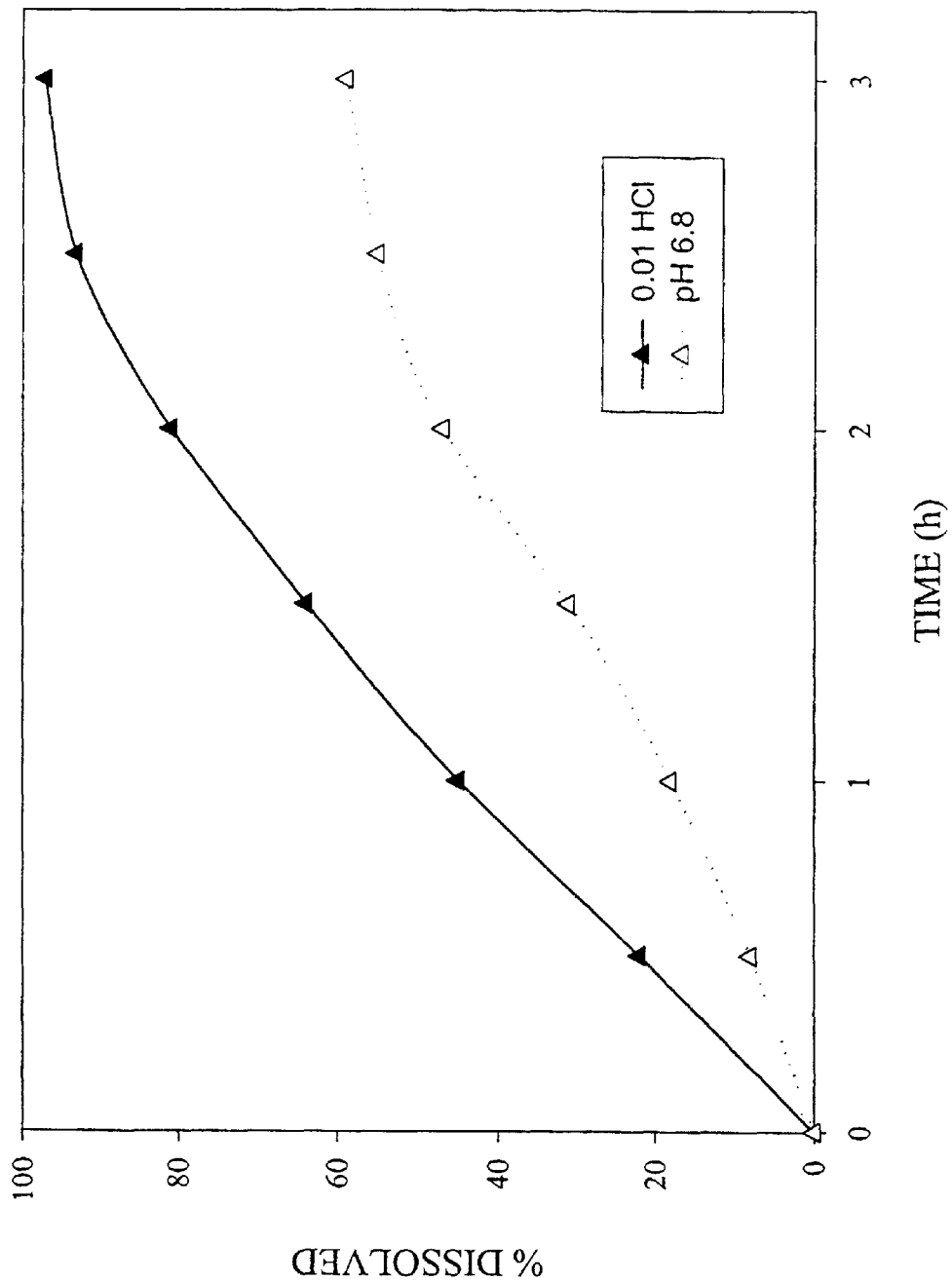
FIG. 4 shows an in vitro dissolution profile of the tablets of comparative example 1, in 0.01 M hydrochloric acid and in pH 6.8 phosphate buffer, as described in comparative example 1.

The results are shown in FIG. 4. They show that prolonged release tablets comprising acid present a profile of dissolution independent from the pH.

EXAMPLE 2

Immediate release tablet comprising 10 mg zolpidem hemitartrate.

Tablets dosed at 10 mg zolpidem hemitartrate and with unitary mass 120 mg were manufactured according to the same method as example 1, having the following composition:

| | |
|---|---|
| zolpidem hemitartrate | 8.3% |
| lactose | 75.8% |
| microcrystalline cellulose[1] | 10.0% |
| hydroxypropylmethylcellulose 606 | 2.1% |
| sodium carboxymethylcellulose[2] | 3.2% |
| magnesium stearate | 0.6% |

[1]Avicel, commercialized by FMC
[2]Primojel, commercialized by Avebe

The dissolution of the tablets was tested according to the method described in example 1, in the 0.01 M hydrochloric acid medium. 90% of the amount of zolpidem contained in the immediate release tablet were released in less than 30 minutes.

Figure 5:
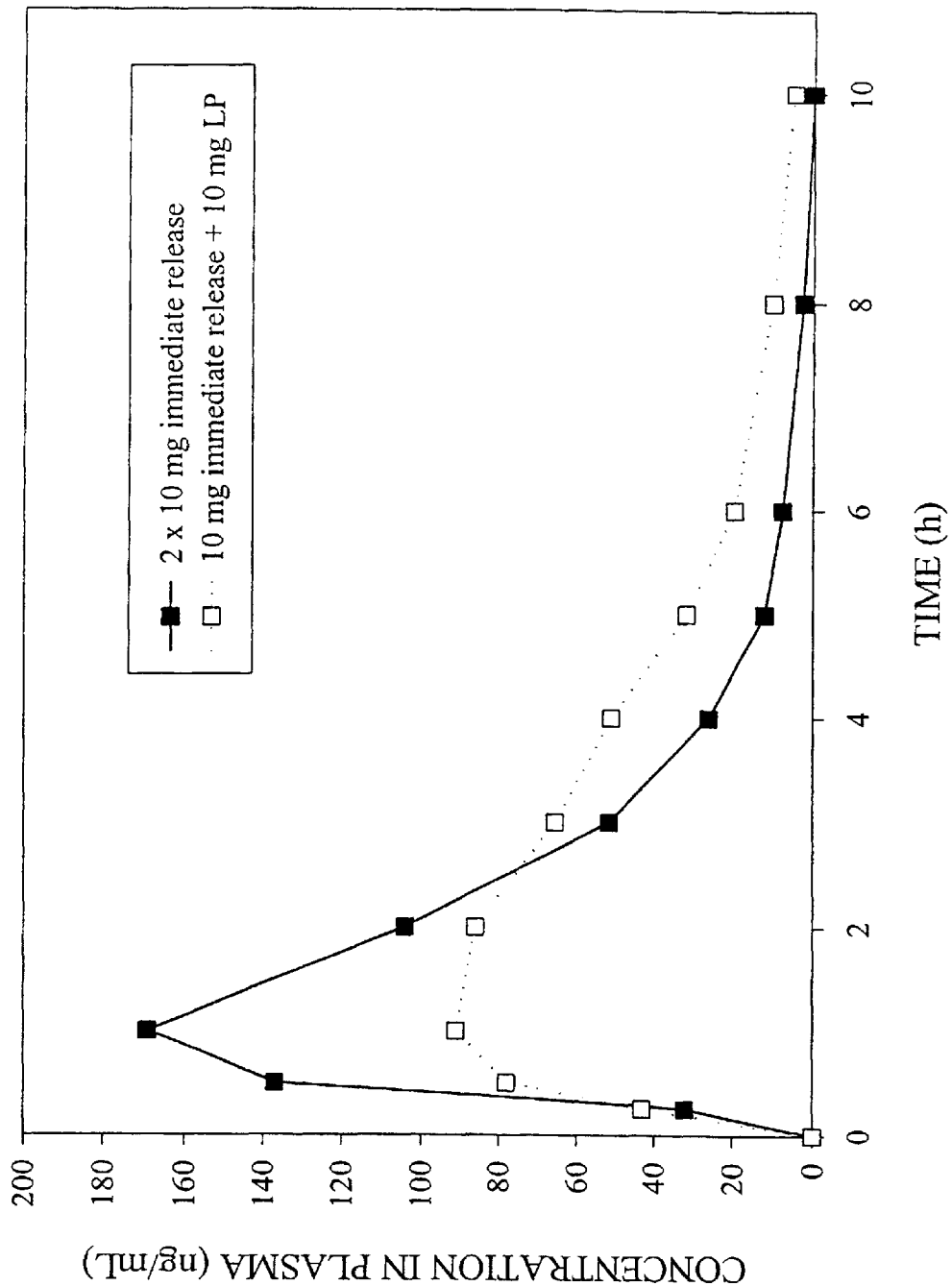
FIG. 5 shows the results of a single dose pharmacokinetic study comparing the immediate tablet formulation of example 2 and the combination of an immediate release tablet and a prolonged release tablet of example 3.

The obtained immediate release tablets were administered orally to 6 healthy volunteers in a pharmacokinetics study. Two tablets were administered orally to each volunteer in a single dose study. Blood samples were taken at 30 min, 1, 2, 3, 4, 6, 8, 10 hours, and analysed for zolpidem. The results (median zolpidem plasma levels) are plotted in FIG. 5 (closed squares).

EXAMPLE 3

Pharmaceutical form consisting of an immediate release tablet comprising 10 mg zolpidem hemitartrate according to example 2, and a prolonged release tablet comprising 10 mg zolpidem hemitartrate according to example 1, within a gelatin capsule.

A pharmacokinetic study of a coadministration of a prolonged release tablet and a immediate release tablet was carried out. One immediate release tablet and one prolonged release tablet each comprising 10 mg zolpidem, as described above were administered to the same 6 volunteers as in the study described in example 2. The results (median zolpidem plasma levels) are plotted in FIG. 5 (open squares). The results show rapid increase in zolpidem levels to give a peak at 30 minutes, the same as for the immediate release, but plasma levels from 3–6 hours after dosing which are higher than those obtained with the same dose (20 mg) of the immediate release formulation. The whole quantity of zolpidem is released in a maximum time of about 8 hours. The dissolution profile was identical to that of the addition of the dissolution profiles of example 1 and 2. Thus the immediate and prolonged release pharmaceutical entities each contained 10 mg zolpidem hemitartrate (50%) and the immediate release phase was 12.2 mg (61%) and the prolonged release phase was 7.8 mg (39%). The complete dissolution time (90% released) was 2 h. The profile parameters are: $T_3=2.12$ h; $T_2=1.19$ h; $(T_2-T_1)=0.43(T_3-T_1)$, the profile being close to zero-order. EXAMPLE 4

Capsule comprising a mixture of immediate release pellets and coated prolonged release pellets.

A suspension comprising 100 g zolpidem hemitartrate and 100 g povidone, commercialized under the reference Plasdone K29/32 by BASF, in 670 g ethanol was prepared. 750 g of this suspension was sprayed onto 1060 g of 16–18 mesh microgranules in a fluid bed drier. Dissolution of zolpidem was tested in 0.01 M hydrochloric acid, according to the method in example 1.80% was dissolved in 2 minutes, and 100% was dissolved at 30 minutes.

Figure 6:
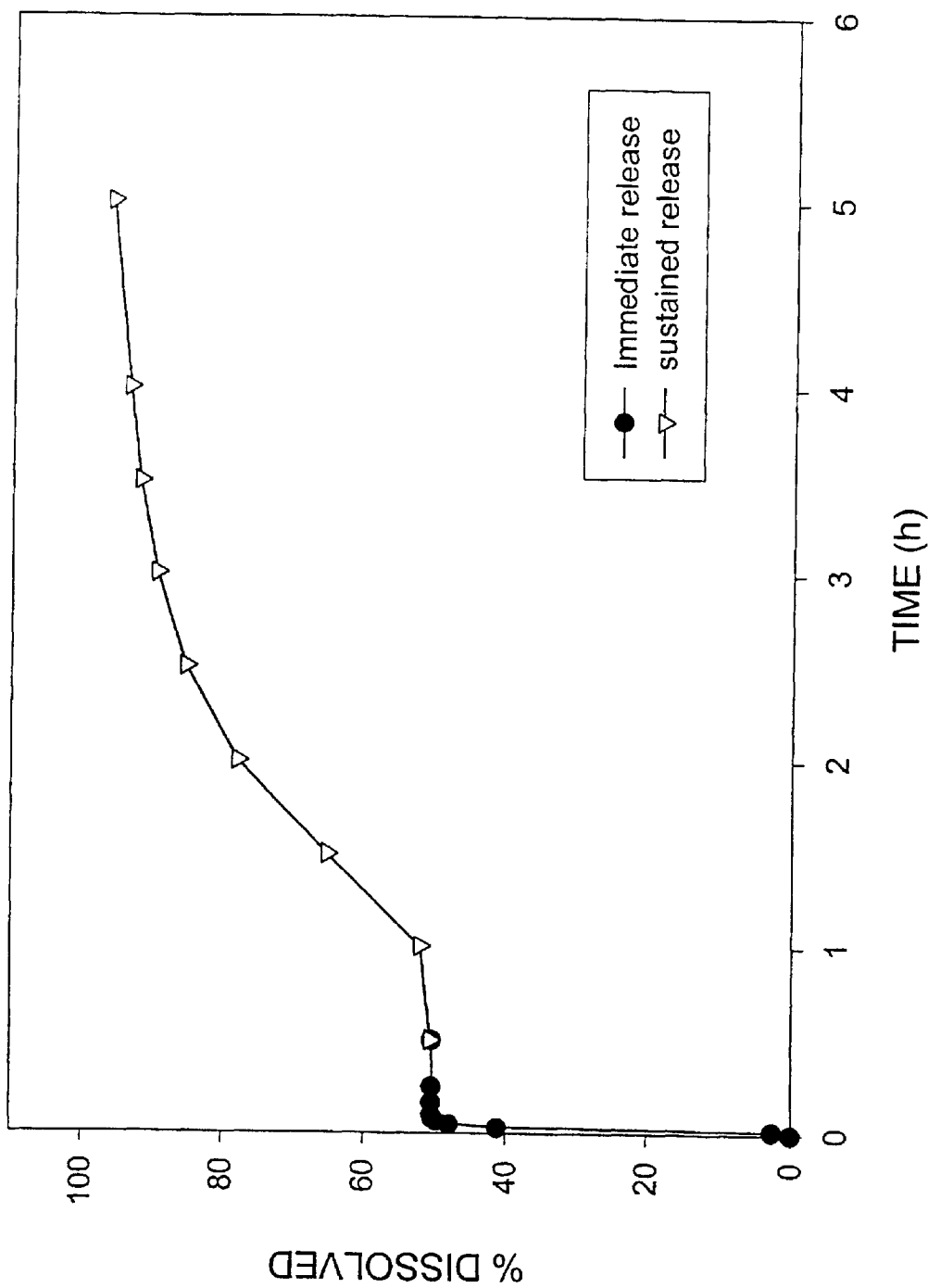
FIG. 6 shows the dissolution profile of a mixture of immediate release and prolonged release spheroids of example 4, in 0.01 M hydrochloric acid.

A solution comprising 25 g of methacrylate copolymer Eudragit® RL100, 143 g of methacrylate copolymer Eudragit® RS100 (both commercialized by Röhm Pharma) and 18.7 g of ethyl citrate commercialized under trademark Eudrafex® by Röhm Pharma as plasticiser, was prepared in 1180 g of a 60:40 m/m isopropanol/acetone mixture. Pellets comprising zolpidem were coated with this polymer mixture, by spraying in a fluid bed dryer, the final amount of coating being 20% by mass of the uncoated pellet mass. After maturation of the pellets at 35° C. for 24 hours, a mixture of these coated pellets and the uncoated pellets previously described was prepared in the proportion 1:1 by zolpidem content, and were filled into gelatin capsules to give a total amount of zolpidem hemitartrate content per capsule of 15 mg (12 mg zolpidem base). The dissolution of capsules was tested by the method of example 1, the resulting profile being shown in FIG. 6.

Thus the immediate and prolonged release pharmaceutical entities each contained 7.5 mg zolpidem hemitartrate (50%). Because of the lag-time of about 1 h before release from the prolonged release entity, the immediate release phase (60%) and the prolonged release phase (40%) corresponded exactly to the entities. The complete dissolution time (90% released) was 3.17 h. The profile parameters are: $T_3=3.17$ h; $T_2=1.68$ h; $(T_2-T_1)=0.44$ $(T_3-T_1)$ and the profile was sigmoid in shape.

EXAMPLE 5

Tablet comprising coated prolonged release pellets comprising 5 mg zolpidem hemitartrate within a fast-disintegrating matrix comprising 7.5 mg zolpidem hemitartrate.

Prolonged release coated pellets were manufactured as described in example 4. The pellets were then spray-coated using the same method with a layer of 20% by mass of microcrystalline cellulose. A granule of the following composition was then prepared, by wet granulation:

| | |
|---|---:|
| zolpidem hemitartrate | 8.4% |
| lactose | 20.0% |
| microcrystalline cellulose[1] | 62.9% |
| hydroxypropylmethylcellulose 606 | 3.0% |
| crospovidone[2] | 5.0% |
| magnesium stearate | 0.7% |

[1]Avicel, commercialized by FMC
[2]Kollidon CL, commercialized by BASF

This was mixed with the coated pellets in the proportion 3 parts of granulate to 2 parts of coated pellets (in terms of zolpidem content) and the mixture compressed into tablets dosed at 12.5 mg zolpidem hemitartrate (equivalent to 10 mg zolpidem base).

EXAMPLE 6

Bilayer immediate/prolonged release tablet comprising 12.5 mg zolpidem hemitartrate.

Granulates were prepared by wet granulation according to the following compositions. The granulating process was that described in example 1:

| | |
|---|---:|
| GRANULATE 1 (Immediate release) | |
| zolpidem hemitartrate | 4.4% |
| lactose 150 mesh | 68.3% |
| microcrystalline cellulose | 20.0% |
| hydroxypropylmethylcellulose 606 | 2.5% |
| sodium carboxymethylcellulose | 3.8% |
| magnesium stearate | 1.0% |
| GRANULATE 2 (prolonged release) | |
| zolpidem hemitartrate | 5.6% |
| lactose 150 mesh | 40.0% |
| microcrystalline cellulose | 20.0% |
| tartaric acid | 8.4% |
| hydroxypropylmethylcellulose[1] | 25.0% |
| magnesium stearate | 1.0% |

[1]Metolose 90SH4000, commercialized by Shin-Etsu

The mixtures were then compressed into bilayer tablets of the form shown in FIG. 7(a) using an alternative tablet press. Each tablet contained 12.5 mg zolpidem hemitartrate, the first immediate release layer with 125 mg of granulate 1 comprising 5.5 mg of zolpidem hemitartrate, and the prolonged release layer with 125 mg granulate 2 comprising 7 mg zolpidem hemitartrate. The in vitro dissolution profiles of the tablets were established using the Apparatus 2 of the United States Pharmacopeia. Three dissolution media were employed: hydrochloric acid 0.01 M, a pH 6.8 potassium phosphate 0.025 M buffer, and a pH 7.5 potassium phosphate 0.015 M buffer. The volume of dissolution medium was 500 ml, maintained at 37±0.50° C. Stirring was by the paddle method (75 rpm). A grill was placed in the bottom of each vessel, to prevent sticking of the tablet to the glass surface. The percentage dissolved was determined by measurement of the UV absorbance at 310 nm (continuous sampling by a peristaltic pump in a closed system). The results are shown in FIG. 8. The dissolution profile is almost independent of pH between pH 1 and 6.8. Zolpidem continues to be released at pH 7.5, though at a significantly reduced rate.

The immediate release entity contained 5.5 mg zolpidem hemitartrate (44%) and the prolonged release entity contained 7.5 mg zolpidem hemitartrate (56%). The complete dissolution time (90% released) was 2.14 h. Because of release from the prolonged release pharmaceutical entity from 0 to 0.5 h, the corresponding immediate release phase was 7.5 mg (60%) and the prolonged release phase was 5 mg (40%). The profile parameters are: $T_3=2.23$ h; $T_2 =1.38$ h; $(T_2-T_1)=0.51(T_3-T_1)$, the profile being zero-order.

Comparative Example 2

Comparison of the dissolution profile of a bilayer immediate/prolonged release tablet comprising 12.5 mg zolpidem hemitartrate with that of an immediate release and a prolonged release tablet of the same composition Granulates were prepared by wet granulation according to the following compositions. The granulating process was that described in example 1:

| GRANULATE 1 (Immediate release) | |
|---|---|
| zolpidem hemitartrate | 6.0% |
| lactose 150 mesh | 66.7% |
| microcrystalline cellulose | 20.0% |
| hydroxypropylmethylcellulose 606 | 2.5% |
| sodium carboxymethylcelluse | 3.8% |
| magnesium stearate | 1.0% |
| GRANULATE 2 (prolonged release) | |
| zolpidem hemitartrate | 4.0% |
| lactose 150 mesh | 55.0% |
| microcrystalline cellulose | 20.0% |
| hydroxypropylmethylcellulose[1] | 20.0% |
| magnesium stearate | 1.0% |

[1]Metolose 90SH4000, commercialized by Shin-Etsu

Figure 9:
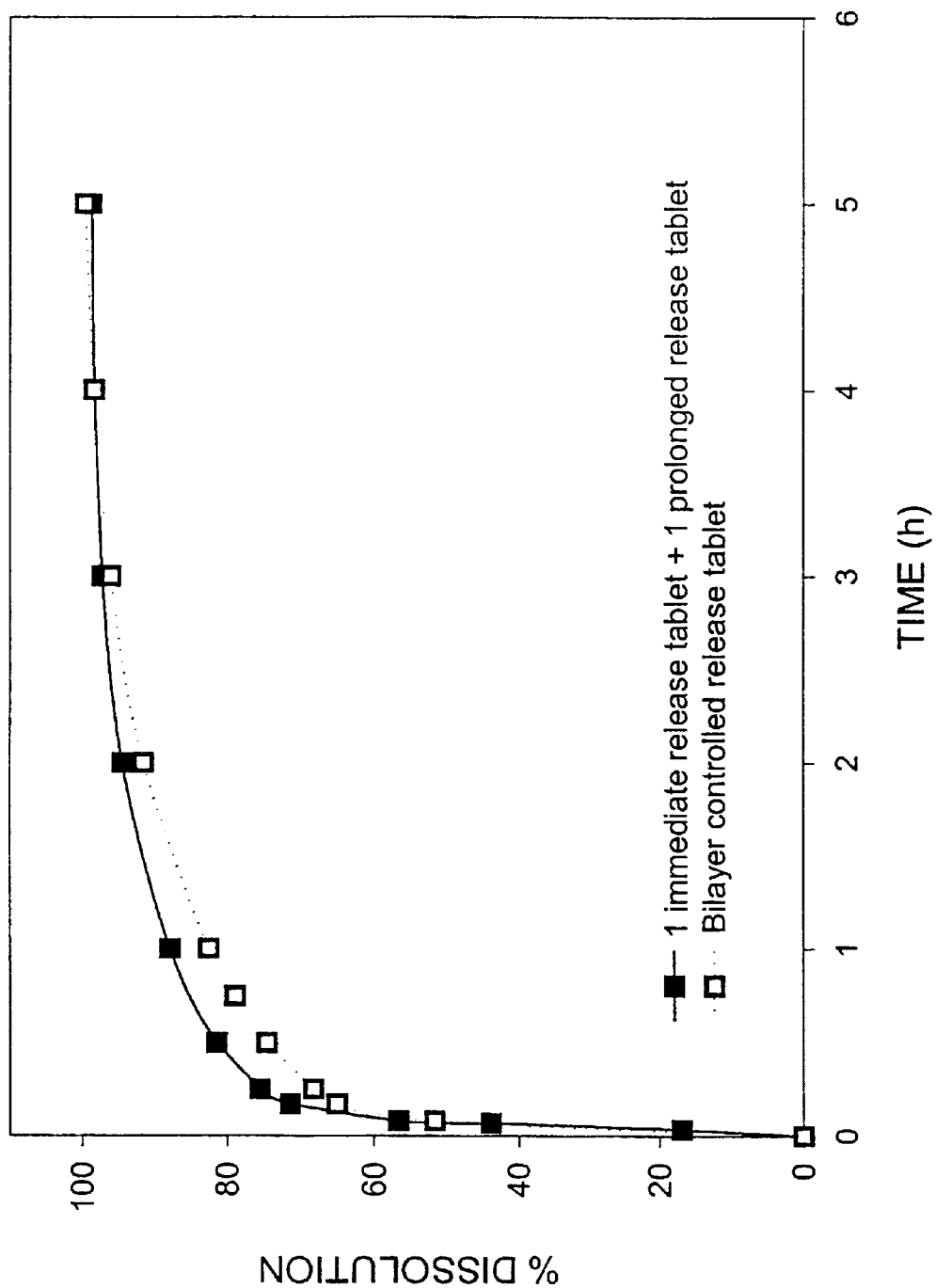
FIG. 9 shows the dissolution profiles of the bilayer tablet and of the combination of an immediate release and a prolonged release tablet of comparative example 2, in 0.01 M hydrochloric acid.

A portion of each granulate was compressed into bilayer tablets of the form shown in FIG. 7(a) using an alternative tablet press. Each tablet contained 12.5 mg zolpidem hemitartrate, the first immediate release layer with 125 mg of granulate 1 comprising 6.5 mg of zolpidem hemitartrate, and the prolonged release layer with 125 mg granulate 2 comprising 6 mg zolpidem hemitartrate. The dissolution profile was tested using the Apparatus 2 of the United States Pharmacopeia. The dissolution medium was hydrochloric acid 0.01 M, maintained at 37±0.5° C. The volume was 500 ml and stirring was by the paddle method (75 rpm). The percentage dissolved was determined by measurement of the UV absorbance at 310 nm (continuous sampling by a peristaltic pump in a closed system). The results are shown in FIG. 9. The pH of the dissolution media had a marked affect on the profile, increased pH depressing the dissolution rate.

The remaining portions of each granulate of comparative example 2 were each compressed into tablets mass 125 mg, the immediate release tablet (granulate 1) comprising 7.5 mg zolpidem hemitartrate, and the prolonged release tablet comprising 5 mg zolpidem hemitartrate. The in vitro dissolution profiles of the tablets were established by the method of example 1.

The resulting profiles are shown on FIG. 9. Surprisingly, the presence of the immediate layer had a significant effect on the dissolution of the hydrophilic matrix prolonged release layer in the bilayer tablet, and whereas the dissolution profile of the separate tablets was the sum of the profiles of the separate tablets, the prolonged release phase of the bilayer tablet was considerably slower than in the case of the separate tablets.

Figure 10:
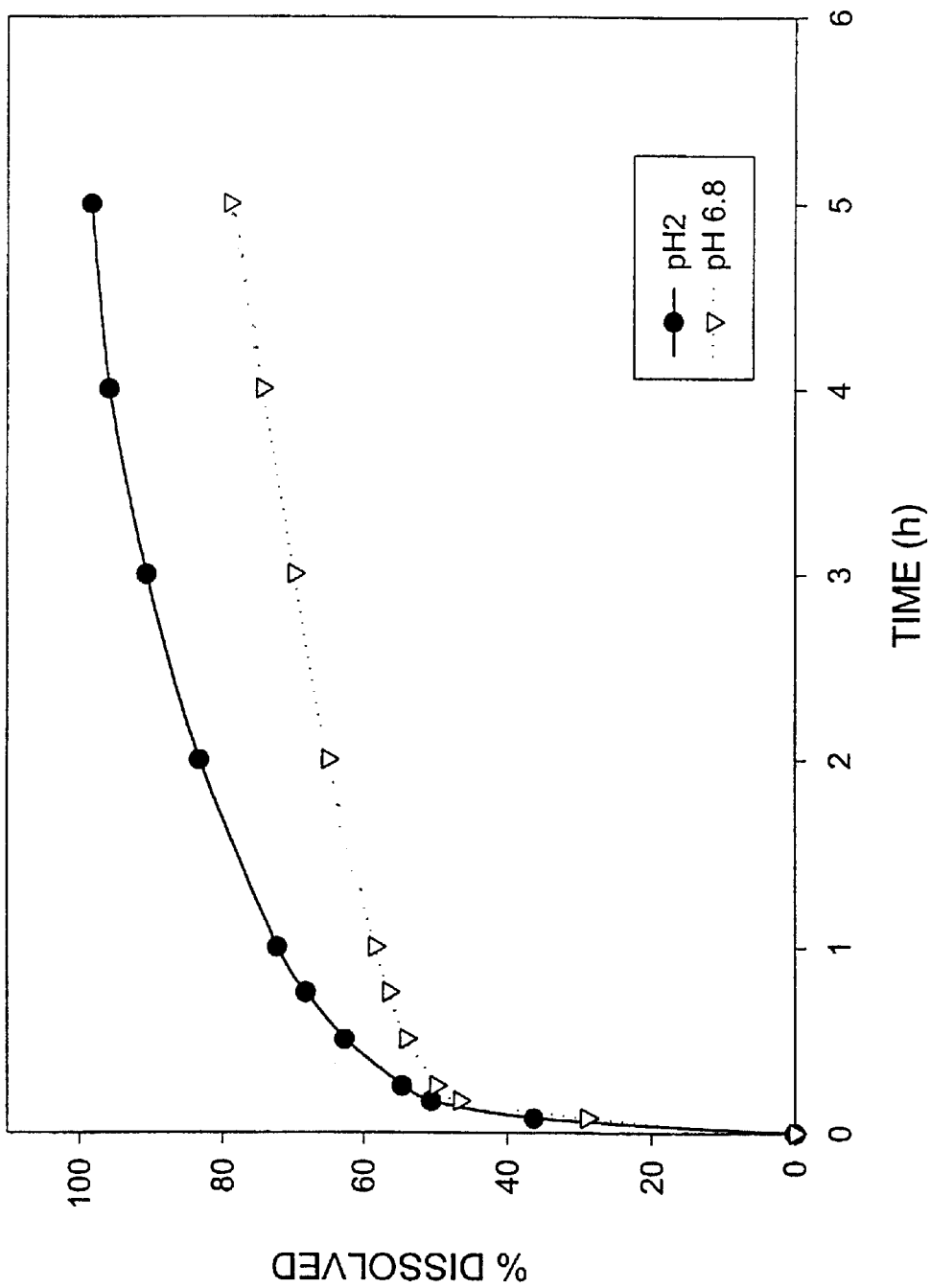
FIG. 10 shows the dissolution profile of the bilayer tablet of comparative example 3, in 0.01 M hydrochloric acid and in pH 6.8 phosphate buffer.

Comparative Example 3 pH dependence of the dissolution profile of a bilayer tablet comprising 12.5 mg zolpidem hemitartrate without acid in the prolonged release layer Granulates similar to those of example 6 were prepared, the only difference being that in the case of granulation 2 (prolonged release) the tartaric acid was missed out and replaced in the formulation by lactose (48.4%). The mixtures were then compressed into bilayer tablets of the form shown in FIG. 7(a) using an alternative tablet press, as for example 6. The in vitro dissolution profiles of the tablets were established as for example 6, using two dissolution media: hydrochloric acid 0.01 M and pH 6.8 potassium phosphate 0.025 M buffer. The results are shown in FIG. 10. The dissolution profile in 0.01 M hydrochloric acid is very close to that of the formulation with acid (example 6), but the rate at pH 6.8 is much decreased.

EXAMPLE 7

Three-layer immediate/prolonged release tablet comprising 12.5 mg zolpidem hemitartrate.

Granulates were prepared by the method of example 1 according to the following compositions:

| LAYER 1 (immediate release) | |
|---|---|
| zolpidem hemitartrate | 5.0% |
| lactose 150 mesh | 67.7% |
| microcrystalline cellulose | 20.0% |
| hydroxypropylmethylcellulose 606 | 2.5% |
| sodium carboxymethylcellulose | 3.8% |
| magnesium stearate | 1.0% |
| LAYER 2 (non-active) | |
| lactose (spray dried) | 60.0% |
| microcrystalline cellulose | 24.0% |
| tartaric acid | 10.0% |
| hydroxyethylcellulose | 5.0% |
| magnesium stearate | 1.0% |
| LAYER 3 (prolonged release) | |
| zolpidem hemitartrate | 6.0% |
| lactose 150 mesh | 40.0% |
| microcrystalline cellulose | 19.0% |
| tartaric acid | 9.0% |
| hydroxypropylmethylcellulose[1] | 25.0% |
| magnesium stearate | 1.0% |

[1]Metolose 905H4000, commercialized by Shin-Etsu

They were compressed as described in example 6 into 3 layer tablets, of the form shown in FIG. 7(d) layer 1 comprising 100 mg of the granulate 1, with 5 mg zolpidem hemitartrate, layer 2 (the middle layer) comprising 100 mg of the granulate 2, and layer 3 comprising 125 mg of the granulate 3 and 7.5 mg zolpidem hemitartrate.

EXAMPLE 8

Coated bilayer immediate/prolonged release tablet comprising 10 mg zolpidem hemitartrate and containing an efferevescent couple and a dye in the immediate release layer.

Mixtures were prepared according to the compositions shown below. The powder mixture 1 for the immediate layer was prepared by dry mixing of the first eight ingredients. the remaining three ingredients are than added. The granulate 2 for the prolonged release layer was prepared by granulation with water of the first five components, the reamining two components being mixed with the granulate after drying and sieving.

| POWDER MIXTURE 1 (Immediate release) | |
|---|---|
| zolpidem hemitartrate | 3.6% |
| anhydrous lactose | 11.3% |
| microcrystalline cellulose | 24.3% |
| povidone K30 | 5.0% |
| tartaric acid | 23.0% |
| sodium bicarbonate | 25.0% |
| sodium carboxymethylcellulose | 3.0% |
| Indigotine W6004 | 0.8% |
| sodium dodecyl sulphate | 2.0% |
| colloidal silica | 1.0% |
| magnesium stearate | 1.0% |
| GRANULATE 2 (prolonged release) | |
| zolpidem hemitartrate | 4.4% |
| lactose 150 mesh | 36.0% |
| tartaric acid | 8.4% |
| microcrystalline cellulose | 20.0% |
| hydroxypropylmethylcellulose[1] | 30.0% |
| colloidal silica | 0.2% |
| magnesium stearate | 1.0% |

[1]Metolose 90SH4000, commercialized by Shin-Etsu

Figure 7:
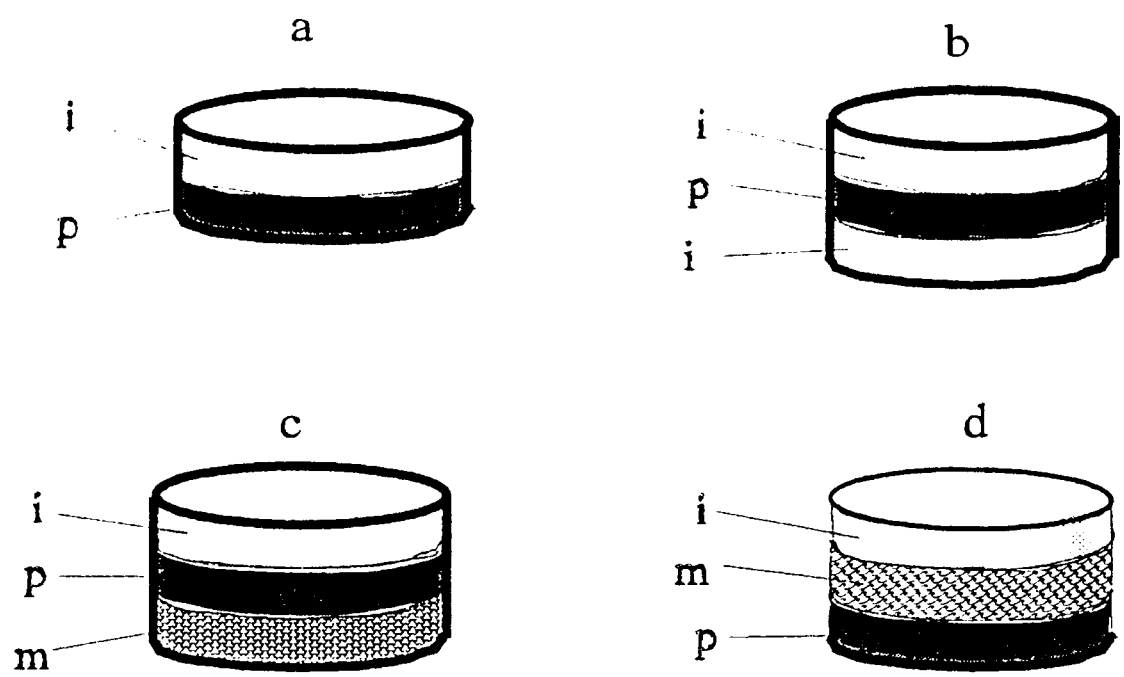
FIG. 7 shows bilayer and multilayer tablets. (a) Bilayer tablet consisting of one immediate release layer and one prolonged release layer. (b) Triple layer tablet consisting of two outer immediate release layers and one inner prolonged release layer. (c) Triple layer tablets consisting of an outer immediate release layer, an inner prolonged release layer, and an outer layer not containing active substance, modulating the release profile. (d) Triple layer tablets consisting of an outer immediate release layer, an outer prolonged release layer, and an inner layer not containing active substance, modulating the release profile.
Figure 8:
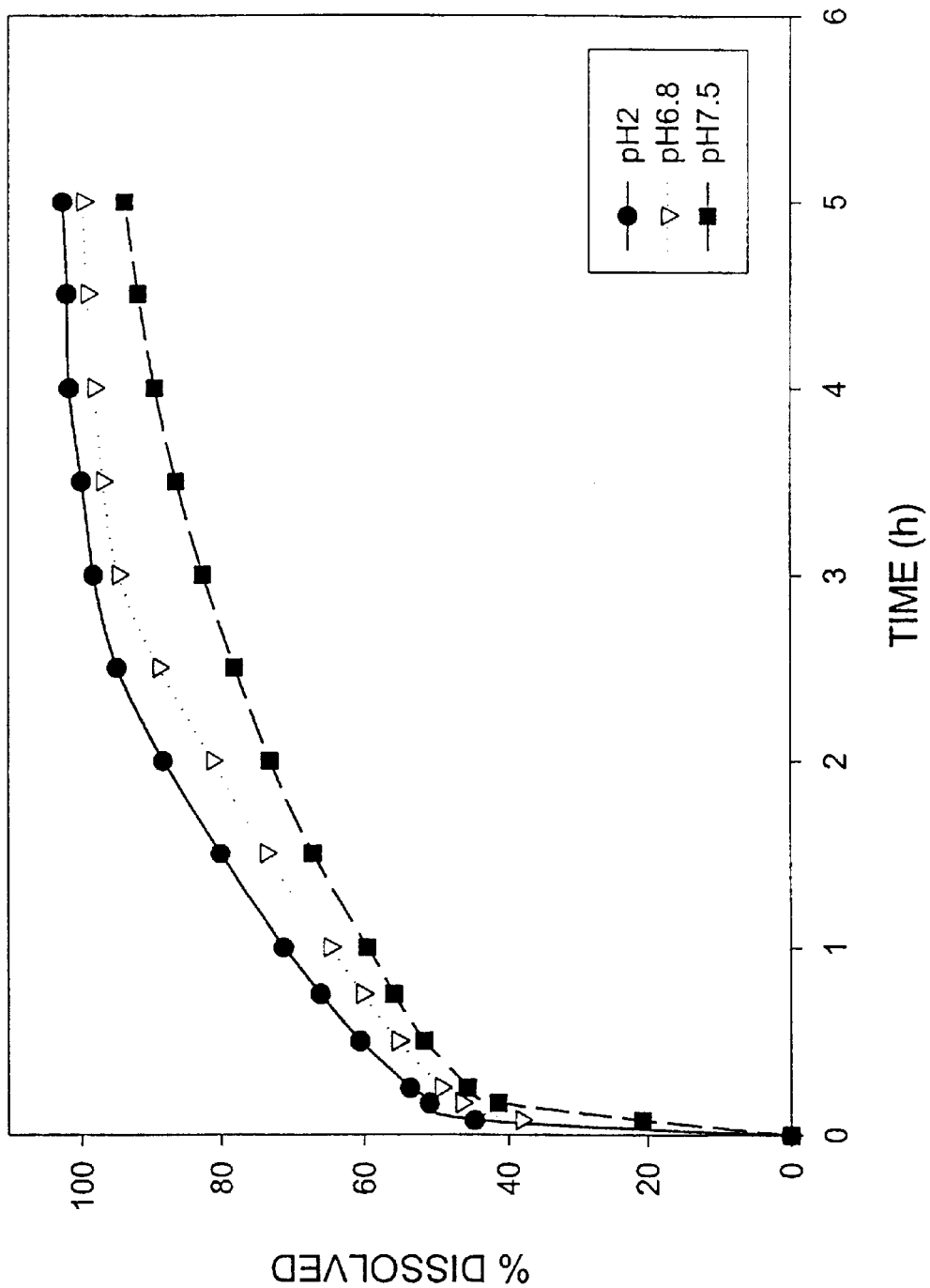
FIG. 8 shows the dissolution profile of the bilayer tablet of example 6, in 0.01 M hydrochloric acid, and in pH 6.8 and pH 7.5 phosphate buffers.

The mixtures were then compressed into bilayer tablets of the form shown in FIG. 7(*a*) using a Manesty BL tablet press. Each tablet contained 10 mg zolpidem hemitartrate, the first immediate release layer with 125 mg of powder mixture 1 comprising 4.5 mg of zolpidem hemitartrate, and the prolonged release layer with 125 mg granulate 2 comprising 5.5 mg zolpidem hemitartrate.

A film coating (4% with respect to tablet mass) of the following composition, was applied as a 20% dispersion in absolute alcohol, using a coating turbine (Glatt GC300).

| copovidone[1] | 12% |
|---|---|
| ethylcellulose | 12% |
| titanium dioxide | 46% |
| Talc | 30% |

[1]Kollidon VA64, commercialized by BASF

Figure 11:
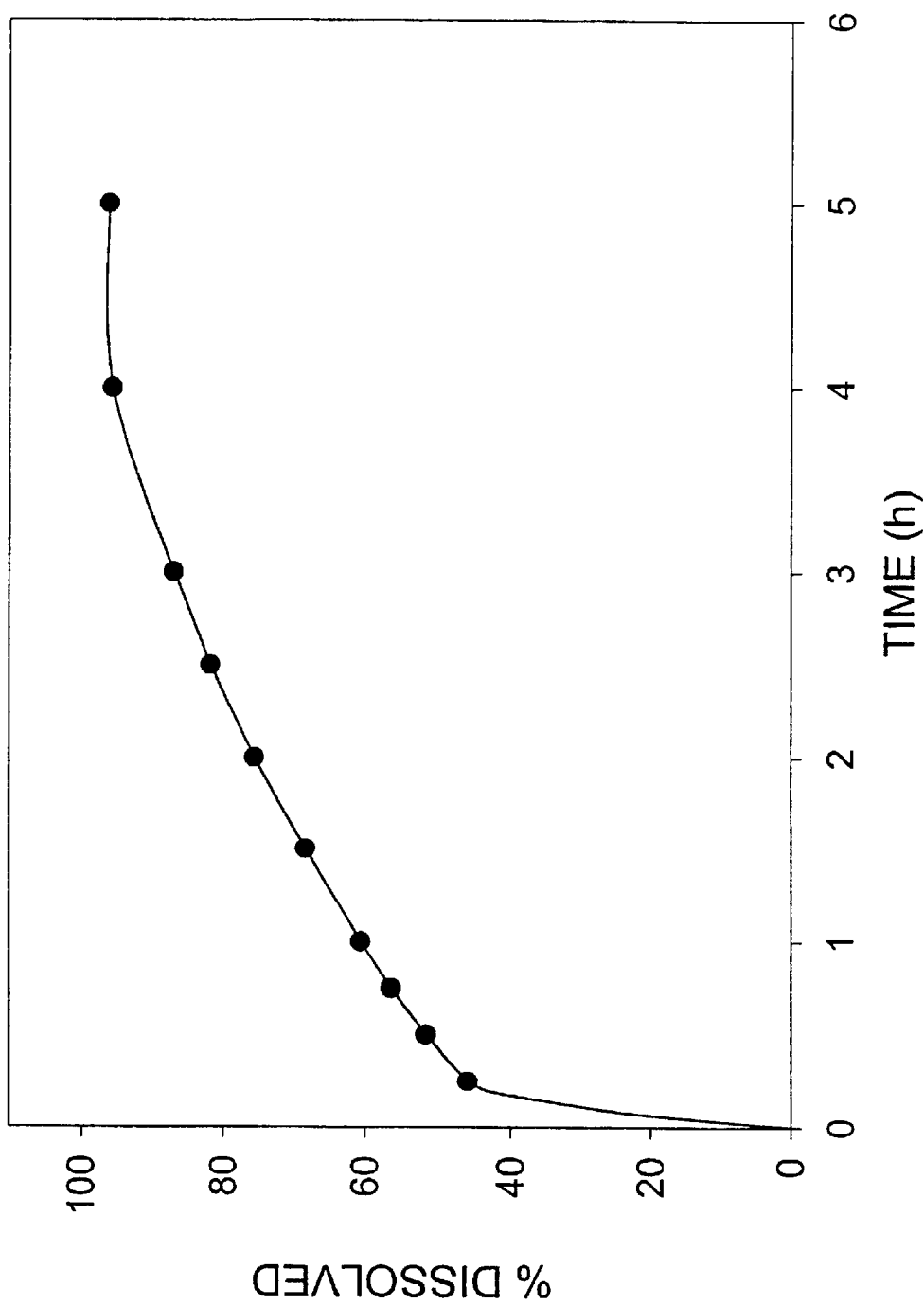
FIG. 11 shows the dissolution profile of the bilayer tablet of example 8, in 0.01 M hydrochloric acid.

The dissolution profile of the tablets was determined in 0.01M hydrochloric acid, using the apparatus and method described in example 6. The results are shown in FIG. 11.

EXAMPLE 9

Coated trilayer immediate/prolonged release tablet comprising 10 mg zolpidem hemitartrate and containing an effervescent couple and a dye.

Mixtures were prepared according to the compositions shown below. The powder mixture 1 for the immediate layer was prepared by dry mixing of the first eight ingredients. the remaining three ingredients are than added. The granulate 2 for the prolonged release layer was prepared by granulation with water of the first five components, the reamining two components being mixed with the granulate after drying and sieving.

| POWDER MIXTURE 1 (Immediate release) | |
|---|---|
| zolpidem hemitartrate | 4.0% |
| microcrystalline cellulose | 36.4% |
| povidone K30 | 5.0% |
| tartaric acid | 23.0% |
| sodium bicarbonate | 25.0% |
| sodium carboxymethylcellulose | 3.0% |
| black iron oxide | 0.3% |
| Indigotine | 0.8% |
| sodium dodecyl sulphate | 1.0% |
| colloidal silica | 1.0% |
| magnesium stearate | 0.5% |
| POWDER MIXTURE 2 (Anti-abuse) | |
| microcrystalline cellulose | 40.4% |
| povidone K30 | 5.0% |
| tartaric acid | 23.0% |
| sodium bicarbonate | 25.0% |
| sodium carboxymethylcellulose | 3.0% |
| black iron oxide | 0.3% |
| Indigotine | 0.8% |
| sodium dodecyl sulphate | 1.0% |
| colloidal silica | 1.0% |
| magnesium stearate | 0.5% |
| GRANULATE 3 (prolonged release) | |
| zolpidem hemitartrate | 4.0% |
| lactose 150 mesh | 36.0% |
| tartaric acid | 8.4% |
| microcrystalline cellulose | 20.4% |
| hydroxypropylmethylcellulose[1] | 30.0% |
| colloidal silica | 0.2% |
| magnesium stearate | 1.0% |

[1]Metolose 90SH4000, commercialized by Shin-Etsu

The mixtures were then compressed into trilayer tablets of the form shown in FIG. 7 (*d*)—the layer not containing zolpidem, that is of granulate 2, being designated by m—using a Manesty BL tablet press. Each tablet contained 10 mg zolpidem hemitartrate. Each layer comprised 125 mg granulate or powder mixture, and the immediate release and prolonged release layers both containing 5 mg of zolpidem hemitartrate.

The tablets were film coated as described in example 8.

EXAMPLE 10

Dry-coated prolonged release tablet dosed at 15 mg zolpidem hemitartrate.

Granulates were prepared with the following composition, using the method described in example 1.

| GRANULATE 1 (Immediate release) | |
|---|---|
| zolpidem hemitartrate | 4.0% |
| lactose 150 mesh | 48.7% |
| microcrystalline cellulose | 40.0% |
| hydroxypropylmethylcellulose 606 | 2.5% |
| sodium carboxymethylcellulose | 3.8% |
| magnesium stearate | 1.0% |
| GRANULATE 2 (prolonged release) | |
| zolpidem hemitartrate | 7.2% |
| lactose 150 mesh | 38.4% |
| microcrystalline cellulose | 20.0% |
| tartaric acid | 8.4% |
| hydroxypropylmethylcellulose[1] | 25.0% |
| magnesium stearate | 1.0% |

[1]Metolose 90SH4000, commercialized by Shin-Etsu

The granulate 2 was compressed using an alternative tablet press to give prolonged release tablets of mass 125 mg dosed at 9 mg zolpidem hemitartrate. The tablets were dry coated with the granulate 1, the mass of dry coating being 150 mg, and the dosage of zolpidem hemitartrate in the coat being 6 mg.

What is claimed is:

1. A pharmaceutical controlled-release dosage form adapted to release zolpidem or a salt thereof over a predetermined time period, according to a biphasic in vitro profile of dissolution when measured in a type II dissolution apparatus according to the U.S. Pharmacopoeia in 0.01M hydrochloric acid buffer at 37° C., where the first phase is an immediate release phase having a maximum duration of 30 minutes and the second phase is a prolonged release phase, and wherein 40 to 70% of the total amount of zolpidem is released during the immediate release phase and the time for release of 90% of the total amount of zolpiderm is between 2 and 6 hours.

2. A pharmaceutical controlled-release dosage form according to claim 1 wherein the second phase has a profile of zero order release.

3. A pharmaceutical controlled-release dosage form according to claim 1 wherein the second phase has a profile where the release is proportional to the square root of the time.

4. A pharmaceutical controlled-release dosage form according to claim 1 wherein the second phase has a profile of first order release.

5. A pharmaceutical controlled-release dosage form according to claim 1 wherein the second phase has a sigmoidal release profile.

6. A pharmaceutical composition comprising zolpidem or a salt thereof in the form of a controlled-release dosage form according to claim 1 wherein said composition comprises an immediate release entity and a prolonged release entity.

7. A pharmaceutical composition according to claim 6 in a dosage form selected from capsules, tablets, multilayer tablets and multicoated tablets.

8. A pharmaceutical composition according to claim 7 in the form of a capsule comprising one or more immediate release tablets and one or more prolonged release tablets.

9. A pharmaceutical composition according to claim 7 in the form of a capsule comprising a mixture of prolonged release pellets and immediate release pellets.

10. A pharmaceutical composition according to claim 7 in the form of a tablet comprising a number of prolonged release coated pellets comprising the drug imbedded in a matrix also comprising the drug.

11. A pharmaceutical composition according to claim 7 in the form of a multilayer tablet comprising:
   (i) one or two prolonged release layers, comprising the drug and a hydrophilic polymer, and
   (ii) one or more immediate release layers comprising the drug.

12. A pharmaceutical composition according to claim 7 in the form of a multicoated tablet comprising:
   (i) a core comprising the drug,
   (ii) a polymer coating layer giving slow release of the drug from this core,
   (iii) a coating layer comprising the drug which is released rapidly or immediately on contact of the dosage form with fluid.

13. A pharmaceutical composition according to claim 6 wherein the immediate release entity and the prolonged release entity are administered simultaneously but separately.

14. A pharmaceutical controlled-release dosage form according to claim 1 containing a pharmaceutically acceptable organic acid selected from tartaric, malic, fumaric, lactic, citric, adipic and succinic acids or their acid salts.

15. A pharmaceutical controlled-release dosage form according to claim 1 capable of generating visual change if it is introduced into a drink, whether or not containing alcohol.

16. A pharmaceutical controlled-release dosage form according to claim 15 wherein the visual change consists of release of coloring excipients, or floating of the dosage form at the surface of the drink, or formation of insoluble particles on the surface of the drink, on the brim of the glass, in the drink and/or on the bottom of the glass or a combination thereof.

17. A pharmaceutical controlled-release dosage form according to claim 16 containing an effervescence generator, a hydrophilic excipient and optionnally a lipophilic excipient and a colouring excipient, in the form of a tablet, a multilayer tablet or a capsule containing controlled release pellets and immediate release pellets or granulates.

18. A pharmaceutical controlled-release dosage form according to claim 1 wherein zolpidem is present as zolpidem hemitartrate.

19. A pharmaceutical controlled-release dosage form according to claim 1 wherein the release rate profile of the second phase is zero order, first order, sigmoidal, proportional to the square root of the time or is intermediate between said profiles.

20. A pharmaceutical composition according to claim 11 wherein the hydrophilic polymer in the one or two prolonged release layers is a cellulose derivative.

21. A pharmaceutical composition according to claim 11 additionally comprising a layer containing hydrophilic polymers but not drug.

22. A pharmaceutical composition according to claim 12 wherein the core contains a pharmaceutically acceptable organic acid.

23. A pharmaceutical composition according to claim 6 wherein the prolonged release entity comprises a pharmaceutically acceptable organic acid selected among tartaric, malic, fumaric, lactic, citric, adipic and succinic acids or their acid salts.

24. A pharmaceutical composition according to claim 22 wherein the prolonged release entity comprises a pharmaceutically acceptable organic acid selected from tartaric, malic, fumaric, lactic, citric, adipic, and succinic acids or their acid salts.

25. A pharmaceutical composition according to claim 6 capable of generating visual change if it is introduced into a drink whether or not containing alcohol.

26. A pharmaceutical composition according to claim 25 wherein the visual change consists of release of included coloring excipients, or floating of the composition at the surface of the drink, a formation of insoluble particles on the surface of the drink, on the brim of the glass, in the drink and/or on the bottom of the glass or a combination thereof.

27. A pharmaceutical composition according to claim 26 containing an effervescence generator, a hydrophilic excipient and optionally a lipophilic excipient and a coloring excipient, in the form of a table, a multilayer tablet or a capsule containing controlled-release pellets and immediate-release pellets or granulates.

28. A pharmaceutical composition according to claim 6 wherin zolpidem is present as zolpidem hemitartrate.

29. A pharmaceutical composition according to claim 28 containing 12.5 mg of zolpidem hemitartrate.

30. A pharmaceutical controlled-release dosage form according to claim 1 containing 4 to 16 mg of zolpidem as zolpidem base.

31. A pharmaceutical composition according to claim 6 containing 4 to 16 mg of zolpidem as zolpidem base.

32. A pharmaceutical composition according to claim 7 in the form of a multilayer tablet comprising an immediate release layer and a prolonged release layer.

33. A pharmaceutical composition according to claim 32 wherein the multilayer tablet is a bi-layer tablet.

34. A pharmaceutical controlled-release dosage form according to claim 18 containing 12.5 mg of zolpidem hemitartrate.

35. A pharmaceutical controlled-release dosage form according to claim 1 wherein the in vitro profile of dissolution is measured in a type II dissolution apparatus according to the U.S. Pharmacopoeia in 0.01M hydrochloric acid buffer at 37° C. stirred at a rate of about 50–75 rpm.

36. A pharmaceutical controlled-release dosage form according to claim 35 containing a pharmaceutically acceptable organic acid selected from tartaric, malic, fumaric, lactic, citric, adipic, and succinic acids or their acid salts.

37. A pharmaceutical controlled-release dosage form according to claim 35 containing 4 to 16 mg of zolpidem as zolpidem base.

38. A pharmaceutical controlled-release dosage form according to claim 35 wherein zolpidem is present as zolpidem hemitartrate.

39. A pharmaceutical controlled-release dosage form according to claim 38 containing 12.5 mg of zolpidem hemitartrate.

40. A pharmaceutical composition comprising zolpidem or a salt thereof in the form of a controlled-release dosage form according to claim 35 wherein said composition comprises an immediate release entity and a prolonged release entity.

41. A pharmaceutical composition according to claim 40 wherein the prolonged release entity comprises a pharmaceutically acceptable organic acid selected from tartaric, malic, fumaric, lactic, citric, adipic, and succinic acids or their acid salts.

42. A pharmaceutical composition according to claim 40 containing 4 to 16 mg of zolpidem as zolpidem base.

43. A pharmaceutical composition according to claim 40 wherein zolpidem is present as zolpidem hemitartrate.

44. A pharmaceutical composition according to claim 43 containing 12.5 mg of zolpidem hemitartrate.

45. A pharmaceutical controlled-release dosage form according to claim 35 wherein the release rate profile of the second phase is zero order, first order, sigmoidal, proportional to the square root of the time or is intermediate between said profiles.

46. A pharmaceutical composition according to claim 40 in the form of a multilayer tablet comprising an immediate release layer and a prolonged release layer.

47. A pharmaceutical composition according to claim 46 wherein the multilayer tablet is a bi-layer tablet.

* * * * *

UNITED STATES PATENT AND TRADEMARK OFFICE
CERTIFICATE OF CORRECTION

PATENT NO.        : 6,514,531 C1                                Page 1 of 1
APPLICATION NO.   : 95/000282
DATED             : August 16, 2013
INVENTOR(S)       : Gérard Alaux et al.

It is certified that error appears in the above-identified patent and that said Letters Patent is hereby corrected as shown below:

In the Specification

In the Inter Partes Reexamination Certificate, at col. 1, lines 6-7, delete "NO AMENDMENTS HAVE BEEN MADE TO THE PATENT" and insert the following:

--THE PATENT IS HEREBY AMENDED AS INDICATED BELOW.--

Col. 11, line 51, replace "phase (60%) and the prolonged release phase (40%)" with:
--phase (50%) and the prolonged release phase (50%)--.

Col. 12, line 66, replace "7.5 mg zolpidem hemitartrate" with --7 mg zolpidem hemitartrate--.

Col. 13, line 39, replace "6.5 mg of zolpidem hemitartrate," with --7.5 mg of zolpidem hemitartrate,--.

Col. 13, line 41, replace "6 mg zolpidem hemitartrate." with --5 mg zolpidem hemitartrate.--.

Signed and Sealed this
Seventeenth Day of June, 2014

Michelle K. Lee
*Deputy Director of the United States Patent and Trademark Office*

US006514531C1

(12) INTER PARTES REEXAMINATION CERTIFICATE (669th)
United States Patent
Alaux et al.

(10) Number: US 6,514,531 C1
(45) Certificate Issued: Aug. 16, 2013

(54) CONTROLLED-RELEASE DOSAGE FORMS COMPRISING ZOLPIDEM OR A SALT THEREOF

(75) Inventors: Gérard Alaux, Beynes (FR); Gareth Lewis, Dourdan (FR); Frédéric Andre, Antony (FR)

(73) Assignee: Sanofi-Aventis, Paris (FR)

Reexamination Request:
No. 95/000,282, Aug. 2, 2007

Reexamination Certificate for:
Patent No.: 6,514,531
Issued: Feb. 4, 2003
Appl. No.: 09/857,154
Filed: Jul. 16, 2001

(21) Appl. No.: 95/000,282

(22) PCT Filed: Dec. 1, 1999

(86) PCT No.: PCT/EP99/10454
§ 371 (c)(1),
(2), (4) Date: Jul. 16, 2001

(87) PCT Pub. No.: WO00/33835
PCT Pub. Date: Jun. 15, 2000

(30) Foreign Application Priority Data

Dec. 4, 1998 (EP) .................................. 98403037

(51) Int. Cl.
*A61K 9/48* (2006.01)
*A61K 9/20* (2006.01)
*A61K 9/50* (2006.01)
*A61K 9/24* (2006.01)
*A61K 31/437* (2006.01)
*A61K 31/4353* (2006.01)
*A61K 31/519* (2006.01)
*A61K 31/496* (2006.01)

(52) U.S. Cl.
USPC .......... 424/468; 424/451; 424/457; 424/464; 424/469; 424/470; 424/471; 424/472; 424/474; 424/489; 424/490

(58) Field of Classification Search
None
See application file for complete search history.

(56) References Cited

To view the complete listing of prior art documents cited during the proceeding for Reexamination Control Number 95/000,282, please refer to the USPTO's public Patent Application Information Retrieval (PAIR) system under the Display References tab.

*Primary Examiner* — Dwayne Jones

(57) ABSTRACT

The present invention relates to controlled-release dosage forms of zolpidem or salts thereof adapted to release zolpidem over a predetermined time period, according to a biphasic profile of dissolution, where the first phase is an immediate release phase and the second phase is a prolonged release phase and particular embodiments thereof intended to avoid abuse.

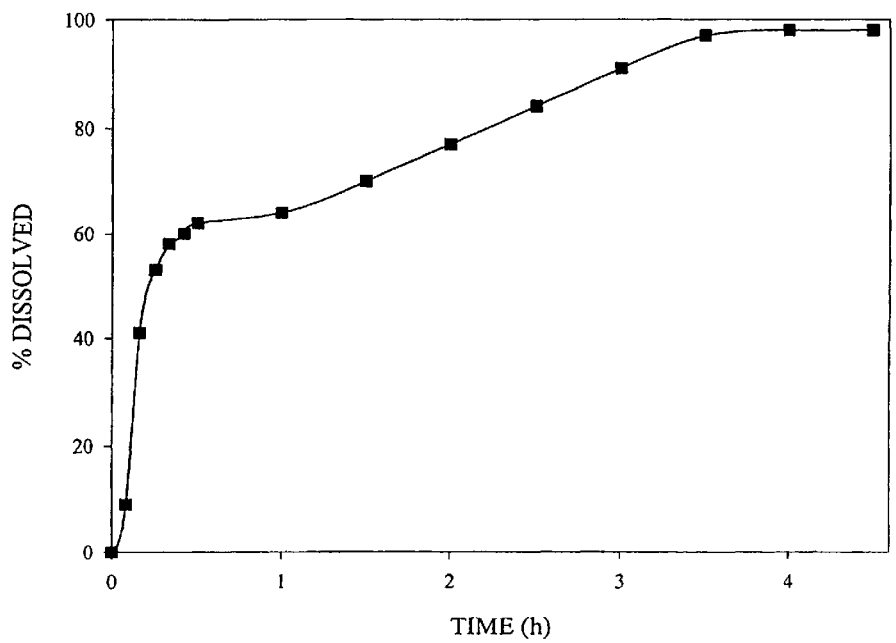

INTER PARTES REEXAMINATION CERTIFICATE ISSUED UNDER 35 U.S.C. 316

NO AMENDMENTS HAVE BEEN MADE TO THE PATENT

AS A RESULT OF REEXAMINATION, IT HAS BEEN DETERMINED THAT:

The patentability of claims 1-47 is confirmed.

\* \* \* \* \*